United States Patent
Woeller et al.

(10) Patent No.: US 7,993,654 B2
(45) Date of Patent: *Aug. 9, 2011

(54) SELF-ADHESIVE POLYMER MATRIX CONTAINING SEA ALGAE EXTRACT

(75) Inventors: Karl-Heinz Woeller, Hamburg (DE); Thorsten Berg, Hamburg (DE); Inge Kruse, Hamburg (DE); Rainer Wolber, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/887,578

(22) Filed: Sep. 22, 2010

(65) Prior Publication Data

US 2011/0076321 A1    Mar. 31, 2011

Related U.S. Application Data

(63) Continuation of application No. 11/157,959, filed on Jun. 22, 2005, now Pat. No. 7,829,099, which is a continuation of application No. PCT/EP03/14793, filed on Dec. 23, 2003, and a continuation-in-part of application No. 11/157,946, filed on Jun. 22, 2005, now Pat. No. 7,820,177, which is a continuation of application No. PCT/EP2003/014792, filed on Dec. 23, 2003.

(30) Foreign Application Priority Data

Dec. 23, 2002 (DE) .................... 102 60 872
Dec. 23, 2002 (DE) .................... 102 60 873

(51) Int. Cl.
  *A61K 36/02* (2006.01)
  *A61K 9/14* (2006.01)
  *A61K 9/70* (2006.01)

(52) U.S. Cl. .............. 424/195.17; 424/487; 424/449; 424/445

(58) Field of Classification Search .......... None
See application file for complete search history.

(56) References Cited

U.S. PATENT DOCUMENTS

| | | | |
|---|---|---|---|
| 3,770,780 A | 11/1973 | Hirsch | |
| 3,790,533 A | 2/1974 | Samour | |
| 3,900,610 A | 8/1975 | McKenna, Jr. | |
| 4,144,325 A | 3/1979 | Voyt | |
| 4,248,861 A | 2/1981 | Schutt | |
| 4,369,180 A | 1/1983 | Mihalovits | |
| 4,978,531 A | 12/1990 | Yamazaki et al. | |
| 5,094,761 A | 3/1992 | Trinh et al. | |
| 5,102,564 A | 4/1992 | Gardlik et al. | |
| 5,194,253 A | 3/1993 | Garrido | |
| 5,234,610 A | 8/1993 | Gardlik et al. | |
| 5,324,718 A | 6/1994 | Loftson | |
| 5,472,954 A | 12/1995 | Loftson | |
| 5,543,157 A | 8/1996 | Trinh et al. | |
| 5,552,378 A | 9/1996 | Trinh et al. | |
| 5,571,782 A | 11/1996 | Trinh et al. | |
| 5,580,851 A | 12/1996 | Trinh et al. | |
| 5,635,238 A | 6/1997 | Trinh et al. | |
| 5,660,845 A | 8/1997 | Trinh et al. | |
| 5,773,029 A | 6/1998 | Chiesi et al. | |
| 5,827,529 A | 10/1998 | Ono et al. | |
| 6,190,689 B1 | 2/2001 | Hoffmann et al. | |
| 6,217,913 B1 | 4/2001 | Mohammadi | |
| 6,335,088 B1 | 1/2002 | Morikane et al. | |
| 6,419,935 B1 | 7/2002 | Gueret | |
| 6,432,431 B1 | 8/2002 | Muta et al. | |
| 6,572,868 B1 | 6/2003 | Cope | |
| 2001/0007671 A1 | 7/2001 | Gueret | |
| 2001/0036783 A1 | 11/2001 | Morikane et al. | |
| 2002/0034525 A1 | 3/2002 | Sakai et al. | |
| 2002/0076387 A1 | 6/2002 | Birkel et al. | |
| 2002/0150616 A1 | 10/2002 | Vandecruys | |

FOREIGN PATENT DOCUMENTS

| | | |
|---|---|---|
| DE | 68915737 | 3/1990 |
| DE | 19646233 | 5/1997 |
| DE | 10051955 | 5/2002 |
| DE | 10054479 | 5/2002 |
| EP | 1172083 | 1/1970 |
| EP | 0303445 | 2/1989 |
| EP | 0392608 | 10/1990 |
| EP | 0507160 | 10/1992 |
| EP | 0579435 | 1/1994 |
| EP | 0970707 | 1/2000 |
| EP | 0976382 | 2/2000 |
| EP | 0756493 | 7/2000 |
| EP | 1097712 | 5/2001 |
| EP | 1136057 | 9/2001 |
| EP | 1158021 | 11/2001 |
| FR | 94777 | 2/1970 |
| FR | 2808195 | 11/2001 |
| JP | 63-208518 | 8/1988 |
| JP | 2-243607 | 9/1990 |
| JP | 4-178323 | 6/1992 |
| JP | 11-228340 | 8/1999 |
| RU | 2158125 | 10/2000 |
| WO | 95/30411 | 11/1995 |
| WO | 98/55148 | 12/1998 |
| WO | 01/02478 | 1/2001 |

OTHER PUBLICATIONS

English language abstract of DE 100 54 479.
English language abstract of RU 2158125.
English language abstract of FR 2808195.
English language abstract of DE 19646233.
English language abstract of JP 06304239 and English language machine translation of JP 06304329.
English language abstract of JP 11-228340.
English language abstract of JP 4-178323.
English language abstract of JP 2-243607.
English language abstract of JP 63-208518.
Donatas Satas "Handbook of Pressure Sensitive Adhesive Technology" 3rd ed. (1999), Satas & Associates, Warwick, RI, pp. 458-461.
Uekama K. et al. "Cyclodextrin Drug Carrier Systems" Chemical Reviews, 1998, vol. 98, pp. 2045-2076.

(Continued)

*Primary Examiner* — Christopher R Tate
*Assistant Examiner* — Randall Winston
(74) *Attorney, Agent, or Firm* — Greenblum & Bernstein, P.L.C.

(57) ABSTRACT

A self-adhesive polymer matrix which comprises a polymer that forms a gel in water, water, a sea algae extract, and a monohydric or polyhydric alcohol.

20 Claims, No Drawings

OTHER PUBLICATIONS

Loftsson T. et al. "Cyclodextrins: New Drug Delivery Systems in Dermatology" International Journal of Dermatology, 1998, vol. 37, pp. 241-246.

Motwani M. et al. "Applications of Cyclodextrins in Skin Products" Cosmetics & Toiletries, vol. 112, Jul. 1997, pp. 39-47.

Citernesi U. et al. "Cyclodextrins in Functional Dermocosmetics", Cosmetics & Toiletries, vol. 110, Mar. 1995, pp. 53-61.

Wallhäusser K. H. "Praxis der Sterilisation Desinfektion—Konservierung", 5$^{th}$ ed., 1995, Georg Thieme Verlag, Stutgart, New York, pp. 469-474.

Quecke K. "Transdermale therapeutische Systeme und ihre Klebstoffproblematik" Kleben & Dichten, Jhrg. 42 (1998), No. 5, p. 26-30.

DW ACC 1988-283016, Aug. 1988, Japan.

Deflandre A. et al. "Photostability Assessment of Sunscreens. Benzylidene Camphor and Dibenzoylmethane Derivatives" International Journal of Cosmetic Science, vol. 10, 1988, pp. 53-62.

Voelckel A. et al. "Vorkommen und Photo-Isomerisierung der Urocaninsäure im Stratum Corneum bei polymorpher Lichtdermatose (PLD). Vergleichende Untersuchung bei PLD-Patienten und Hautgesunden" Zentralblatt Haut- und Geschlechtskrankheiten, Springer-Verlag, vol. 156, 1989, pp. 1-15.

Miyachi Y. "Skin Diseases Associated with Oxidative Injury" in "Oxidative Stress in Dermatology", edited by Fuchs J., Packer L., Marcel Dekker, Inc. New York, Basel, Hong Kong, 1993, pp. 323-331.

Zviak C. "Hair Coloring—Nonoxidation Coloring" and "Oxidation Coloring" in "The Science of Hair Care", Marcel Dekker, Inc., 1986, pp. 235-286.

Elias P. M. "Structure and Function of the Stratum Corneum Permeability Barrier" Drug Development and Research, vol. 13, 1988, pp. 97-105.

SELF-ADHESIVE POLYMER MATRIX CONTAINING SEA ALGAE EXTRACT

CROSS-REFERENCE TO RELATED APPLICATIONS

The present application is a continuation-in-part of U.S. patent application Ser. No. 11/157,959, filed Jun. 22, 2005, the entire disclosure whereof is expressly incorporated by reference herein, which is a continuation of International Application No. PCT/EP2003/014793, filed Dec. 23, 2003, the entire disclosure whereof is expressly incorporated by reference herein, which claims priority under 35 U.S.C. §119 of German Patent Application No. 102 60 873.3, filed Dec. 23, 2002, and also is a continuation-in-part of U.S. patent application Ser. No. 11/157,946, filed Jun. 22, 2005, the entire disclosure whereof is expressly incorporated by reference herein, which is a continuation of International Application No. PCT/EP2003/014792, filed Dec. 23, 2003, the entire disclosure whereof is expressly incorporated by reference herein, which claims priority under 35 U.S.C. §119 of German Patent Application No. 102 60 872.5, filed Dec. 23, 2002.

BACKGROUND OF THE INVENTION

1. Field of the Invention

The present invention relates to a self-adhesive polymer matrix composed of a polymer which is gel-forming in water, preferably a polyacrylic acid polymer, water, sea algae extract, and a monohydric or polyhydric alcohol. The matrix may be doped with hydrophilic or else hydrophobic active substances.

2. Discussion of Background Information

The mechanism of action of patches for administering pharmaceutical substances into the skin is subject to a functional principle similar to that of transdermal therapeutic systems (TTS).

Transdermal therapeutic systems for delivering active substances into and/or through the skin have been known for a long time and constitute patch-like systems which in particular are doped with drugs.

The topical administration of drugs via active substance patch systems offers two main advantages:

First, this administration form produces first-order release kinetics of the active substance, thereby allowing a constant level of active substance to be maintained in the body over a very long period of time.

Secondly, the path of uptake through the skin avoids the gastrointestinal tract and also the first pass through the liver. As a result, selected drugs can be administered effectively in a low dose. This is particularly advantageous when it is desired that the drug should act locally, avoiding a systemic effect. This is the case, for example, with the treatment of rheumatic joint complaints or muscular inflammation.

The time-dependent release of the substance, the drug for example, from a TTS takes place in dependence on its TTS/skin partition coefficient and its diffusion in the region of the TTS and of the skin.

Both factors are determined by the composition of the matrix, thereby allowing the amount released per unit time and the duration of activity to be influenced directly. Normally hydrocolloids, solubilizers and enhancers are used for this purpose, allowing improved solubility and diffusion and also a more rapid passage of the substance from a TTS into the skin.

Ideally, first-order release kinetics are achieved, allowing the release of equal quantities per unit time.

One embodiment of such transdermal systems which has been well described in the technical literature is that of matrix systems or monolithic systems in which the drug is incorporated directly into the pressure-sensitive adhesive. In the ready-to-apply product a pressure-sensitive adhesive matrix of this kind, comprising active substance, is equipped on one side with a backing, which is occlusive for the active substance, while on the opposite side there is a backing film equipped with a release layer, which is removed prior to application to the skin (kleben&dichten, No. 42, 1992, pp. 26 to 30).

The aforementioned properties of a TTS avoid the need for frequently repeated administration and avoid burdening the skin with high concentrations of active substances, and so reduce irritation to the skin, which is unavoidable in the event of repeated administration of liquid and semisolid administration forms. If, nevertheless, unwanted effects occur in the course of a TTS application, further burdening can be halted immediately by removing the TTS.

In summary, the advantages of the TTS lie in a distinctly improved compliance on the part of users, which is attributable to the simple and rapid administration and to the long-lasting efficacy of transdermal therapeutic systems.

One basic requirement of a TTS is effective adhesion to skin, which must be maintained over the entire period of the intended dosing of active substance, and another is the ability for the TTS to be removed without residue. Painful redetachment of the active substance patch after a prolonged period of wear is a frequent observation. As well as adhesives which are coated in solution onto the backing, the adhesives used also include solvent-free systems, such as hot-melt adhesives. A feature of these adhesives is that in the course of their coating it is possible to forego the use of organic solvent and dispersion medium. Hot-melt adhesives are converted to a liquid form by heating and are applied thus as a melt to the respective patch backing. As well as technical aspects, such as solvent processing, plant design with anti-explosion measures, and environmental protection strictures, medical reasons as well play a part in the choice of solvent-free adhesives.

Transdermal therapeutic systems are generally applied to healthy, intact skin. Here in particular it is especially important not to irritate, let alone damage, the skin by a drug product. One frequently observed side-effect is the appearance of skin irritations, which appear in particular when a TTS is applied for a prolonged period, or repeatedly, to the same region of the body. Irritations of this kind are caused primarily by the ingredients of the pressure-sensitive adhesive matrix. In the case of solvent-borne systems it is possible following the extraction of the solvents to recover a residual amount, which on the basis of its allergenic potential may likewise lead to unwanted skin irritations. For application to skin, therefore, solvent-free systems whose formulations include, in particular, skin-friendly ingredients are to be preferred above all.

Self-adhesive matrix systems for administering active pharmaceutical and/or cosmetic substances are among traditional applications in Asia, particularly in Japan, and are defined in the Japanese pharmacopoeia under the terms "cataplasm". Cataplasms, accordingly, are commonly prepared by mixing glycerin, water or other suitable liquids with finely pulverized active substances, with the addition of essential oils.

Glycerin functions here as a humectant, in order to prevent the cataplasms from drying out prematurely in use.

Whereas in the traditional Asian preparations natural thickeners such as alumina, etc., are employed, recent decades have seen the use, more and more, of modern synthetic raw materials, such as polyacrylic acid as a gel former, for example, for their production. This allows the cataplasms, which are commonly pasty, to be produced as hydrogel matrices having improved attractiveness and user-friendliness.

EP 1 136 057 describes an aqueous gel system for cosmetic use without backing or liner, with a light transmittance of min. 70%.

EP 0 507 160 describes cataplasms containing lidocaine.

A disadvantage of the cataplasms described is that the production of the base matrices requires many different individual components such as gel formers, thickeners, plasticizers, humectants, stabilizers, emulsifiers, pH regulators, antioxidants, etc., and possibly also solubilizers and penetration enhancers in the case of active substance cataplasms. Since the adhesive performance and consistency of such a matrix is a function of the interaction of all of the individual components, targeted product development/optimization with regard to these fundamental product requirements is, correspondingly, time-consuming and arduous.

The production of polymer matrices, especially gel matrices, from polyacrylates has likewise been known for many years and is described for example in. EP 0 507 160, JP 11-228340 and JP 04178323. Gel matrices are used, among other things, as an adhesive base and as an active substance reservoir in transdermal systems. Such systems have an adequate bond strength, especially to moist skin (buccal patches), but because of inadequate cohesiveness cannot be removed again completely when required.

In order to form a gel with a defined structure it is necessary for polyacrylic acid to be cross-linked. The nature of the cross-linker makes a critical contribution to the structure of the resultant gel. The customary cross-linking agents may be metal ions (e.g.: $Al^{3+}$ ions), or organic compounds. Cross-linking with aluminum salts proceeds via the coordination of the oxygen functions of the polyacrylic acid to the $Al^{3+}$ ions. A very close-meshed gel with high viscosity is formed, the viscosity of the gel being controllable only via the amount of cross-linker (Handbook of Pressure Sensitive Technology, page 458 ff, 1999).

JP 11-228340 discloses polyacrylic acid-based gels which utilize $Al^{+3}$ compounds as cross-linkers. The use of the mandatory aluminum compound as a cross-linking agent is limited, since otherwise the physical properties of the gel are impaired. If the proportion of aluminum cross-linker is too high the gel becomes too hard.

Known from the literature are further examples of cross-linking with polyvalent metal ions, e.g., U.S. Pat. No. 3,900,610 (zinc salts), U.S. Pat. No. 3,770,780 or U.S. Pat. No. 3,790,533 (titanium compounds). Ionic cross-linking with metal ions leads to hard, viscous polymer gels with low tack (Handbook of Pressure Sensitive Adhesive Technology, page 458 ff, 1999).

EP 303445 discloses a patch with a monolithic gel matrix based on water-soluble polymers. Mandatory constituents are clebopride or a pharmaceutically acceptable salt thereof as active substance, water, water absorbers, and water-soluble polymers. As water-soluble polymers the skilled worker is able to select from a range of known polymers such as polyvinyl alcohol, gelatin, polyacrylic acid, sodium polyacrylates, methylcellulose, carboxymethylcellulose, polyvinylpyrrolidone, rubber and other cross-linkable polymers and also mixtures thereof.

EP 976382 describes a patch comprising a matrix composed of a system which is hydrophilically gelling in aqueous phase and which is formed from gelan gum and at least one further hydrocolloid. Gelan gum is claimed mandatorily. Gelan gum is understood by the skilled worker, as defined by technical dictionaries, to comprise hydrocolloids obtained from the following marine plants: *Agardhiella tenera, Furcellaria fastigiata, Hypnea cervicornis, musciformis, spicifera, Suhria vitata*. The term does not comprise sea algae extracts. Nor is there any mention of the essential aspects of self-adhesive properties, the adjustability of bond strength and elasticity of the resultant matrices.

A further problem associated with the cross-linking of polyacrylic acid to form a self-adhesive matrix or gel is that a matrix once produced, having defined physical properties, viscosity, tack, etc., must have the same defined properties in a later production operation. This reproducibility is difficult if not impossible to realize with the cross-linking technologies that are presently known.

It would be desirable to provide a simple polymer matrix system for cataplasms/hydrogels which, with a few ingredients, allows matrices of defined consistency and bond strength to be produced in a controlled fashion.

It would likewise be advantageous to be able to provide a polymer matrix in which water-soluble or hydrophobic active substances can be incorporated and can be delivered to the skin in a controlled fashion.

It would further be desirable to provide patches which comprise aforementioned polymer matrices and can be used as TTS.

SUMMARY OF THE INVENTION

The present invention provides a self-adhesive polymer matrix which comprises (a) at least one polymer which forms a gel in water, (b) water, (c) a sea algae extract, and (d) at least one alcohol which is a monohydric or polyhydric alcohol.

In one aspect of the polymer matrix, component (a) may comprise a polyacrylic acid polymer. By way of non-limiting example, the polyacrylic acid polymer may comprise an acrylate-alkyl acrylate copolymer with the structure:

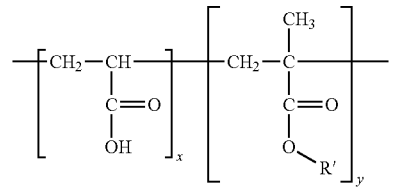

where R' is an alkyl radical and x and y indicate the stoichiometric fraction of the respective comonomers and/or may comprise a copolymer of a $C_{10-30}$ alkyl acrylate and acrylic acid, methacrylic acid and/or esters thereof, which copolymer is crosslinked with an allyl ether of sucrose or with an allyl ether of pentaerythritol.

In another aspect, the polymer matrix may comprise from 2% to 55% by weight of component (a), based on the total weight of the matrix, e.g., at least 5% by weight and/or not more than 30% by weight of component (a).

In yet another aspect of the polymer matrix of the present invention, component (c) may comprise agar-agar and/or carrageenan and/or alginic acid and/or a salt or ester of alginic acid. In another aspect, component (c) may be present in a concentration of 0.1% to 15% by weight, based on the total weight of the matrix, e.g., in a concentration of at least about 0.5% by weight and/or not more than 5% by weight.

In a still further aspect of the polymer matrix of the present invention, component (d) may comprise glycerin and/or propanediol, preferably glycerin. In another aspect, component (d) may be present in a concentration of from 1% to 85% by weight, based on the total weight of the matrix, e.g., in a concentration of at least 5% by weight and/or not more than 45% by weight.

In another aspect, the polymer matrix of the present invention may further comprise (e) at least one pharmaceutically active substance and/or a cosmetic or dermatological substance. For example, component (e) may comprise one or more active substances selected from dexpanthenol, capsaicin, lidocaine and salts thereof, menthol, camphor, ibuprofen and salts thereof, such as lysinate, ketoprofen, eucalyptus oil, peppermint oil, chlorhexidine and thereof, silver or silver compounds, jojoba oil and aloe vera, and/or a disinfectant and/or an antiseptic and/or component (e) may comprise at least one of creatine, creatinine, alpha-glucosylrutin, taurine, serinol, isoserinol, liquorice aqua PU, liquorice PU, silymarin, silyphos, lipoic acid, liponamide, green tea extract, vitamin C, 8-hexadecene-1,16-dicarboxylic acid, isoflavone, isoflavonoid-containing plant extracts, ubiquinone Q10, sericosides, tyrosine sulfate, jojoba oil, and aloe vera.

In yet another aspect, the matrix may comprise up to 35% by weight, e.g., not more than 15% by weight of component (e), based on the total weight of the matrix.

The present invention also provides a self-adhesive polymer matrix that comprises from 2% to 55% by weight of (a) at least one polymer which forms a gel in water, (b) water, from 0.1% to 15% by weight of (c) a sea algae extract, and from 1% to 85% by weight of (d) at least one alcohol which is a monohydric or polyhydric alcohol, each based on the total weight of the matrix.

In one aspect, component (a) may comprise at least one polyacrylic acid polymer, component (c) may comprise agar-agar and/or carrageenan, preferably agar-agar, and component (d) may comprise glycerin and/or the matrix may comprise from 5% to 30% of component (a), from 0.5% to 5% by weight of component (c), and from 5% to 45% by weight of component (d).

In another aspect, the polymer matrix may further comprise up to 15% by weight of (e) one or more pharmaceutical active substances, based on the total weight of the matrix. For example, the matrix may further comprise up to 15% by weight of one or more of dexpanthenol, capsaicin, lidocaine and salts thereof, menthol, camphor, ibuprofen and salts thereof, ketoprofen, eucalyptus oil, peppermint oil, chlorhexidine and thereof, silver or silver compounds, jojoba oil and aloe vera and/or up to 15% by weight of at least one substance that is a disinfectants and/or an antiseptic.

The present invention also provides a two-dimensional product that comprises the polymer matrix set forth above, including the various aspects thereof, and has a total area of from 0.2 to 1000 cm$^2$, as well as a two-dimensional or three-dimensional product which comprises from 0.1 to 1,000 g, e.g., 500 g, of the polymer matrix.

The present invention also provides a medical patch, a bandage and a wound covering, each of which comprises the polymer matrix set forth above, including the various aspects thereof.

The present invention also provides a wound care method which comprises the application of a product which comprises the polymer matrix set forth above to a wound.

The present invention also provides a method of soothing sensitive or irritated skin, which method comprises the application of a product which comprises the polymer matrix set forth above to the sensitive or irritated skin.

The present invention also provides a method of administering an active substance, which method comprises the application of the active substance in the polymer matrix set forth above to a body surface. For example, the polymer matrix may be applied topically or buccally and/or the polymer matrix may be a component of a transdermal therapeutic system, e.g., a monolithic transdermal therapeutic system.

The present invention also provides a method of treating a skin burn, which method comprises the application of the polymer matrix set forth above, which matrix comprises menthol, to at least parts of the skin burn.

The present invention also provides a method of treating disorders of the rheumatic type, which method comprises the application of the polymer matrix set forth above, which matrix comprises a nonsteroidal antirheumatic, to a body surface.

The present invention also provides a method of alleviating a cold-type disease, which method comprises the application of the polymer matrix set forth above, which matrix comprises an essential oil, to a body surface.

The present invention also provides an aromatherapy method, which method comprises the application of the polymer matrix set forth above, which matrix comprises an essential oil, to a body surface.

The matrix is composed of a polymer which forms a gel in water, preferably a polyacrylic acid gel, as a bond-strength-determining component. The sea algae extract may, for example, be agar-agar. As alcohol use is made in particular of monohydric or polyhydric alcohols, preferably glycerin, which act as consistency factors. Despite the fact that the individual components are known for use for producing cataplasms or hydrogels, it was not hitherto known to employ agar-agar in conjunction with glycerin, for example, specifically as consistency factors for polyacrylic acid matrices.

An increase in the fraction of sea algae extract in polymer matrices, such as cataplasms/hydrogels, increases the strength of the matrices. However, it also increases the stiffness and reduces the tack. This disadvantage can be compensated by adding alcohol, especially glycerin. It is therefore possible to set a desired elasticity in the resultant polymer matrix in conjunction with a constant fraction of sea algae extract.

Accordingly, a synergistic combination of sea algae extract and monohydric or polyhydric alcohols, preferably glycerin, ensures a desired elasticity in the gel matrices.

The basis for its use as a consistency factor is that sea algae extract, in contrast to, in particular, the widespread gelatin and other consistency factors, does not induce gelling in conjunction with alcohols, such as glycerin or propanediol, for example. Since monohydric or polyhydric alcohols according to the invention, such as glycerin or propanediol, are distributed homogeneously in water but do not form gels with the sea algae extract, alcohols of this kind hence act as an elasticity factor for the matrices.

Another example of a sea algae extract for use in the present invention is carrageenan. Carrageenan is a hydrophilic polysaccharide of high molecular weight which is obtained from various red algae, principally *Chondrus crispus*, by hot-water extraction, subsequent freezing and following cleaning. The structure of carrageenan is composed primarily of repeating units of galactose and 3,6-anhydrogalactose, both in sulfated and unsulfated form. The principal distinction between kappa, iota and lambda carrageenan is the number and position of the ester sulfate groups on the repeating galactose units.

Gelling of carrageenan is possible only in the presence of cations. Preference in accordance with the invention is given to kappa and iota carrageenan, which form gels in the presence of calcium ions (kappa and iota), potassium ions and ammonium ions (kappa only). Particularly advantageous is the use of corresponding cation hydroxides, since the polyacrylic acid likewise used for producing gel matrix systems of the invention must be neutralized in order to form stable gels.

Carrageenan is available industrially from, for example, Lehmann & Voss & Co. under the names Gelcarin, Viscarin and Seaspen.

Another example of a sea algae extract for use in the present invention is alginic acid as well as salts (alginates) and esters thereof. The most common salts of alginic acid are the sodium and calcium salts, although other salts such as ammonium and potassium alginate are commercially available as well. Examples of commercially available esters of alginic acid are, for example, propylene glycol alginate and siloxanetriol alginate.

Alginic acid is present in the cell walls of brown algae (Phaeophyceae) in the form of its calcium, magnesium and sodium salts. Starting materials for recovering alginic acid and its salts are, for example, *Macrocystis pyrifera, Ascophyllum* spp., *Laminaria* spp., *Sacophyllum* spp. and *Sargassum* spp. The algae are usually first washed with dilute acid and then extracted with alkali, e.g., by stirring them with a hot solution of sodium carbonate. Over a period of about two hours, the alginate dissolves as sodium alginate to give a thick slurry. After separation from the insoluble components (mainly cellulose) the sodium alginate is converted into a precipitate in the form of alginic acid (by adding acid) or calcium alginate (by adding a water-soluble calcium salt such as calcium chloride). The precipitated product can then be further processed and converted into a derivative of alginic acid such as, e.g., a different salt or an ester.

Sea algae extract such as agar-agar is a hydrophilic colloid of polysaccharide structure composed of the gelling agarose and the non-gelling agaropectin, which is obtained from various marine algae of the Rhodophyceae class by hot-water extraction, subsequent freezing and following cleaning. Agar-agar is available industrially from, for example, Riedel de Haen AG.

The sea algae extract, for example, agar-agar, carrageenan, and alginic acid and/or salts and esters thereof, is used preferably in an amount of 0.1%-15% by weight, more preferably between 0.5%-5% by weight. All percentages here are based on weight fractions of the polymer matrix, unless indicated to the contrary.

Monohydric or polyhydric alcohols such as, for example, glycerin (1,2,3-propanetriol) are pharmaceutical industrial auxiliaries that enjoy widespread use, inter alia, as solubilizers or humectants.

Monohydric or polyhydric alcohols, such as glycerin, for example, are used in accordance with the invention with preference in an amount of 1%-85% by weight, more preferably between 5%-45% by weight.

The fraction of polymer which forms a gel in water, such as a polyacrylic acid gel, for example, in the matrix governs the adhesion. In contrast to agar-agar, polyacrylic acid forms gels both with water and with alcohols, so that the adhesion set by the fraction of polyacrylic acid remains constant independently of the particular alcohol fraction.

Polyacrylates that are advantageous in accordance with the invention are acrylate-alkyl acrylate copolymers, particularly those chosen from the group of what are called carbomers or carbopols (Carbopol® is a registered trademark of the B. F. Goodrich Company). In particular the acrylate-alkyl acrylate copolymer or copolymers that is or are advantageous in accordance with the invention is or are characterized by the following structure:

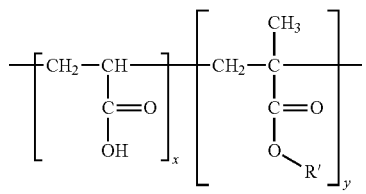

In this structure R' is an alkyl radical, in particular a long-chain alkyl radical, and x and y are numbers which symbolize the respective stoichiometric fraction of the respective comonomers.

Acrylate copolymers and/or acrylate-alkyl acrylate copolymers that are particularly preferred in accordance with the invention are those available under the commercial designations Carbopol® 1382, Carbopol® 981 and Carbopol® 5984 from the B. F. Goodrich Company, preferably polyacrylates from the group of the Carbopols of types 980, 981, 1382, 2984 and 5984, and more preferably Carbomer 2001.

Advantageous further are copolymers of $C_{10\text{-}30}$ alkyl acrylates and one or more monomers of acrylic acid, of methacrylic acid or of esters thereof, which are cross-linked with an allyl ether of sucrose or with an allyl ether of pentaerythritol.

The polymer which forms a gel in water, especially polyacrylic acid and/or copolymers thereof, is used preferably in an amount of 2%-55% by weight, or preferably between 5%-30% by weight.

The polymer matrices are prepared without the use of organic solvents, preferably at 40-95° C., in standard commercial mixers/compounders or, continuously, in suitable extruders.

A further suitable polymer which gels in water is inter alia baobab flour.

In this way it is possible, using only water, polymer which forms a gel in water, sea algae extract, and monohydric or polyhydric alcohol as starting materials, to produce, in a targeted fashion, soft, smooth, self-adhesive hydrogel matrices as a basis for production and use as patches, TTS, cataplasms or pads.

In order to produce particular performance properties it is possible for the polymer matrices to be admixed with appropriate plasticizers, solubilizers, penetration enhancers, neutralizing agents such as tromethamol (2-amino-2-(hydroxymethyl)-1,3-propanediol), triethanolamine (2,2',2"-nitrilotriethanol) or NaOH, for example, fillers and/or other known additives, although it is not mandatory to add them.

The gel matrix can thus be doped with hydrophilic active substances, or else, in the case of an appropriate solubilizer, with hydrophobic active substances, for wound healing or skin care. In the case of incorporation of hydrophobic active substances it may be of benefit to use cyclodextrins for encapsulation.

Cyclodextrins (cycloamyloses, cycloglucans) are known per se in cosmetic and pharmaceutical preparations.

Improving the solubility of substances of sparing solubility, in the presence of cyclodextrins in an aqueous medium, has been described for individual substances. Advantageous may be both the inclusion compounds of a substance, also called the guest, with a cyclodextrin species—in this context both 1:1 or 1:2 complexes and complexes with other molar ratios (guest:cyclodextrin) are possible—and the physical mixtures thereof.

The cyclodextrins are cyclic oligosaccharides composed of α-1,4-linked glucose units. In general, six to eight glucose units (α-, β-, or γ-cyclodextrin) are joined to one another.

Cyclodextrins are obtained when starch is acted on by *Bacillus macerans*. They possess a hydrophobic interior and a hydrophilic exterior. By virtue of their structure, cyclodextrins and their derivatives are able to form inclusion complexes. They are suitable for the "molecular encapsulation" of active substances (e.g., as a protective envelope around sensitive molecules in cosmetic and pharmaceutical formulations).

These applications are also described in a series of patents (e.g., WO 98/55148, EP 0 579 435, EP 0 392 608). In these publications, however, usually only one active substance is complexed by the cyclodextrin (derivative). While multicomponent inclusion complexes are described in EP 0756 493, when looked at more closely the latter relates to a salt and not to a two-component mixture of acid and base.

In the following the phrase "cyclodextrin and/or a derivative thereof" refers both to cyclodextrins having different numbers of glucose units in the ring molecule, and to derivatives of these compounds.

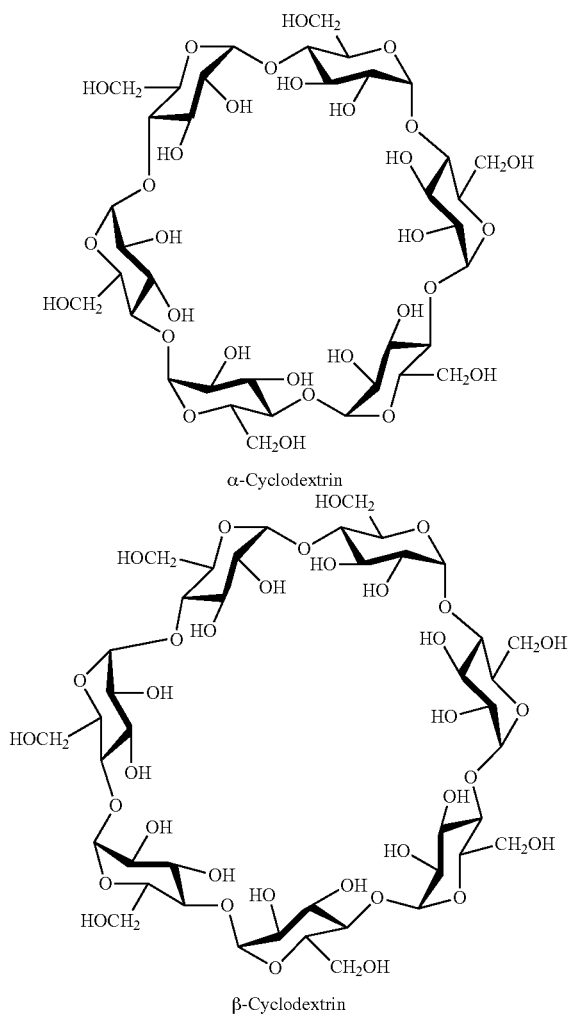

α-Cyclodextrin

β-Cyclodextrin

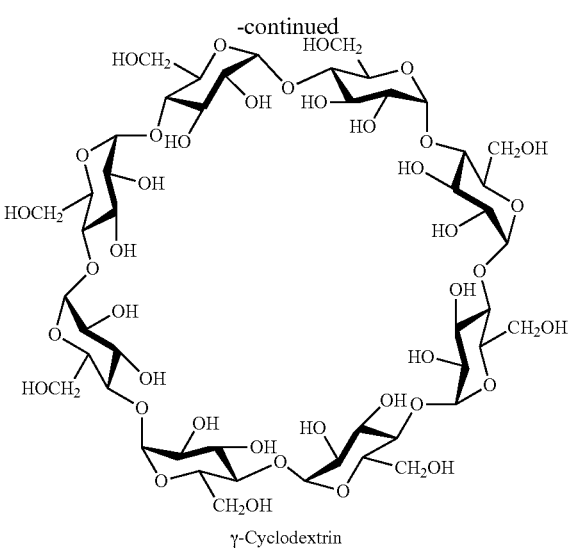

γ-Cyclodextrin

In accordance with the invention the cyclodextrin or cyclodextrins is or are used preferably in cosmetic or dermatological compositions in a concentration of 0.0005% to 20.0% by weight, in particular 0.01% to 10% by weight, and more preferably in a concentration of 0.1% to 5.0% by weight.

It is advantageous in accordance with the invention to use native cyclodextrins or cyclodextrins with polar and/or apolar substitution. These include preferably, but not exclusively, methyl-, especially random-methyl-β-cyclodextrin, ethyl- and also hydroxypropyl-cyclodextrins, such as HP-β-cyclodextrin or HP-γ-cyclodextrin, for example.

The cyclodextrin species that are particularly preferred in accordance with the invention are γ-cyclodextrin and also hydroxypropyl-β-cyclodextrin.

Further prior art is contained in the following publications:
K. Uekama et al., Chemical Reviews, 1998, 98, 2045-2076, "Cyclodextrin drug carrier systems"
T. Loftsson, Int. J. Dermatology, 1998, 37, 241-246, "Cyclodextrins: new drug delivery systems in dermatology".
J. Zatz et al. Cosmetics & Toiletries, 1997, 112, July, p. 39ff, "Applications of cyclodextrins in skin products".
U. Citernesi, Cosmetics & Toiletries, 1995, 110, March, p. 53 ff, Cyclodextrins in functional dermocosmetics.

The cyclodextrins and/or cyclodextrin-guest inclusion complexes and/or the cyclodextrin substance mixtures used in accordance with the present invention can be incorporated into the polymer matrix without difficulties.

In one embodiment which is particularly preferred in accordance with the invention the polymer matrix or gel matrix comprises active pharmaceutical substances for controlled local or systemic delivery to/into the skin, in amounts of 0-35% by weight, preferably 0-15% by weight.

Examples of active substances which can be used include essential oils. By essential oils are meant plant-derived concentrates which as natural raw materials are used primarily in the fragrance and foodstuffs industries and are composed more or less of volatile compounds. Examples of these compounds that may be mentioned include 1,8-cineol, limonene, menthol, borneol and camphor. The term "essential oils" is often used for the volatile constituents still present in the plants. In their true sense, however, essential oils are understood to be mixtures of volatile compounds prepared by steam distillation from plant raw materials.

Essential oils are composed exclusively of volatile components, whose boiling points are in general between 150 and 300° C. They include predominantly hydrocarbons or monofunctional compounds such as aldehydes, alcohols, esters, ethers and ketones. Parent compounds are mono- and sesquiterpenes, phenylpropane derivatives and longer-chain aliphatic compounds.

In some essential oils, one constituent is dominant (for example, eugenol in clove oil, at more than 85%), while other essential oils constitute complex mixtures of the individual constituents. Often the organoleptic properties are determined not by the main components but by subsidiary or trace constituents, such as, for example, by the 1,3,5-undecatrienes and pyrazines in galbanum oil. The number of identified components in many of the commercially significant essential oils is up into the hundreds. Very many constituents are chiral, with very often one enantiomer being predominant or being present exclusively, such as (−)-menthol in peppermint oil or (−)-linalyl acetate in lavender oil, for example.

Preferred essential oils that may be mentioned include oleum eucalypti, oleum menthae piperitae, oleum camphoratum, oleum rosmarini, oleum thymi, oleum pini sibricum and oleum pini silvestris, and the terpenes 1,8-cineol and levomethanol.

Further essential oils that may be mentioned include oleum abietis albae, oleum anisi, oleum aurantii floris, oleum bargarmottae, oleum calendulae infusum, oleum camphoratum, oleum caryophylli, oleum chamomillae, oleum cinnamomi ceylanici, oleum citri, oleum citronellae, oleum cupressi, oleum cymbopogonis, oleum jecoris, oleum lavendulae, oleum macidis, oleum majoranae, oleum melaleucae viridiflorae, oleum melissae, oleum menthae arvensis, oleum menthae piperatae, oleum millefolium, oleum myrrhae, oleum myrte, oleum oregani, oleum pini sibricum, oleum pinisilvestris, oleum salviae, oleum santali, oleum terebinthinae rectificat, oleum thymi, oleum valerianae, oleum zingiberis and/or tea tree oil.

Peppermint oils are essential oils obtained by steam distillation from leaves and blossoms of various varieties of peppermint, and occasionally also those from Mentha arvensis.

Citrus oils are essential oils obtained from the peel of citrus fruits (bergamot, grapefruit, lime, mandarin, orange, lemon), often also called agrumen oils.

Citrus oils are composed largely of monoterpene hydrocarbons, principally limonene (exception: bergamot oil, which contains only about 40%).

Menthol can be used for example for surface anesthesia in cases of skin irritation as a result of light burns. The products used in this way generate a pleasant feeling of cold and can be used for cooling minor burns that do not require specialist medical treatment.

Menthol has three asymmetric C atoms and accordingly exists in four diastereomeric pairs of enantiomers (cf. the formulae; the other four enantiomers are the corresponding mirror images).

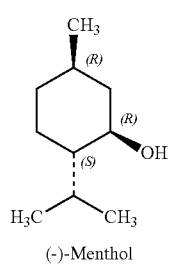

(−)-Menthol
(1)

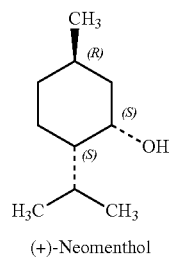

(+)-Neomenthol
(2)

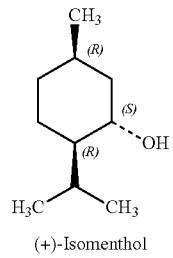

(+)-Isomenthol
(3)

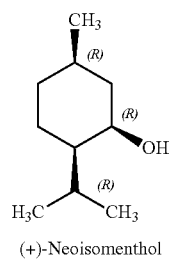

(+)-Neoisomenthol
(4)

The diastereoisomers, which can be separated by distillation, are referred to as neoisomenthol, isomenthol, neomenthol [(+) form: a constituent of Japanese peppermint oil] and menthol. The most important isomer is (−)-menthol (levomenthol), shining prisms with a strong peppermint-like odor.

As further active substances it is possible to add camphor, for example, to the matrix in order to treat rheumatic pain, neuralgias and inflammation. By camphor is meant 2-bornanone, 1,7,7-trimethylbicyclo[2.2.1]heptan-2-one; see diagram below.

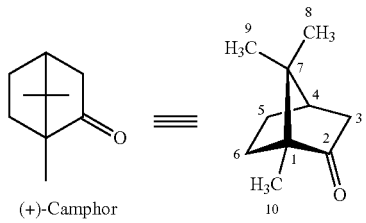

(+)-Camphor

In combination with substances having care properties, however, such as jojoba oil or aloe vera, the polymer matrix of the invention can be used as well. Depending on the definition of their application, such combinations may make a cosmetic out of a drug product, and so drastically shorten the time to market, owing to the reduction in approval times.

For advantageous embodiments of hydrogels/cataplasms of the invention it is also possible, additionally, to mention active hyperemic substances such as natural active substances of cayenne pepper or synthetic active substances such as nonivamide, nicotinic acid derivatives, preferably benzyl nicotinate or propyl nicotinate, and anti-inflammatories and/or analgesics.

By way of example mention may be made of capsaicin

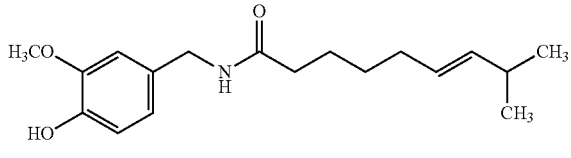

[8-Methyl-trans-6-nonenoic acid (4-hydroxy-3-methoxybenzyl amide)]

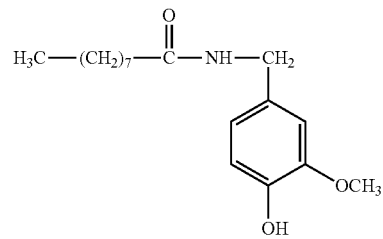

Nonivamide
Nicotinic acid benzyl ester

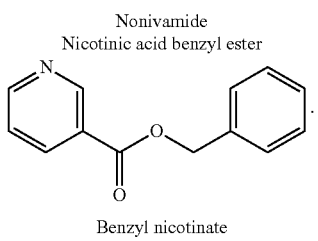

Benzyl nicotinate

Flavone and its derivatives (often also collectively called "flavones") are also advantageous additives in the sense of the present invention. They are characterized by the following basic structure (substitution positions indicated):

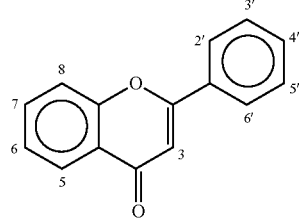

Some of the more important flavones, which can also be used with preference in preparations of the invention, are listed in the table below:

| | OH substitution positions | | | | | | | |
|---|---|---|---|---|---|---|---|---|
| | 3 | 5 | 7 | 8 | 2' | 3' | 4' | 5' |
| Flavone | − | − | − | − | − | − | − | − |
| Flavonol | + | − | − | − | − | − | − | − |
| Chrysin | − | + | + | − | − | − | − | − |
| Galangin | + | + | + | − | − | − | − | − |
| Apigenin | − | + | + | − | − | − | + | − |
| Fisetin | + | − | + | − | − | + | + | − |
| Luteolin | − | + | + | − | − | + | + | − |
| Kampferol | + | + | + | − | − | − | + | − |
| Quercetin | + | + | + | − | − | + | + | − |
| Morin | + | + | + | − | + | − | + | − |

| | OH substitution positions | | | | | | | |
|---|---|---|---|---|---|---|---|---|
| | 3 | 5 | 7 | 8 | 2' | 3' | 4' | 5' |
| Robinetin | + | − | + | − | − | + | + | + |
| Gossypetin | + | + | + | + | − | + | + | − |
| Myricetin | + | + | + | − | − | + | + | + |

In nature, flavones occur ordinarily in glycosylated form.

In accordance with the invention the flavonoids are preferably chosen from the group of substances of the generic structural formula

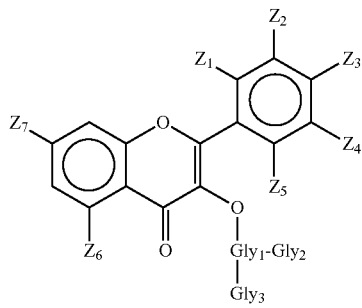

where $Z_1$ to $Z_7$ are chosen independently of one another from H, OH, alkoxy- and also hydroxyalkoxy-, where the alkoxy and hydroxyalkoxy groups respectively may be branched and unbranched and may have 1 to 18 C atoms, and where Gly is chosen from mono- and oligoglycoside residues.

In accordance with the invention the flavonoids can, however, also be chosen advantageously from substances of the generic structural formula

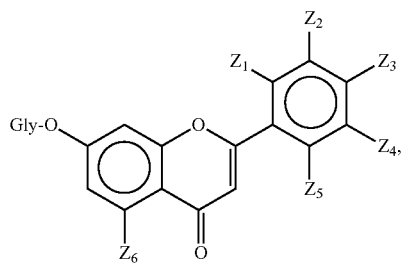

where $Z_1$ to $Z_6$ are chosen independently of one another from H, OH, alkoxy- and also hydroxyalkoxy-, where the alkoxy and hydroxyalkoxy groups respectively may be branched and unbranched and may have 1 to 18 C atoms, and where Gly is chosen from mono- and oligoglycoside residues.

Such structures can be chosen with preference from substances of the generic structural formula

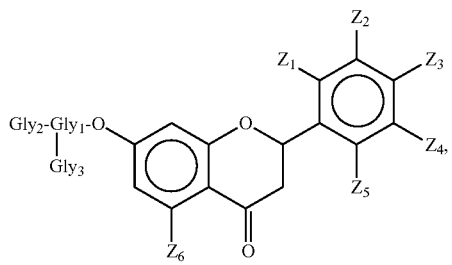

where $Gly_1$, $Gly_2$ and $Gly_3$ independently of one another represent monoglycoside residues or $Gly_2$ and/or $Gly_3$ may also, individually or together, represent saturations by hydrogen atoms.

Preferably $Gly_1$, $Gly_2$ and $Gly_3$ are chosen independently of one another from hexosyl radicals, particularly the rhamnosyl radicals and glucosyl radicals. However, other hexosyl radicals can as well be used with advantage where appropriate, examples being allosyl, altrosyl, galactosyl, gulosyl, idosyl, mannosyl and talosyl. It may also be of advantage in accordance with the invention to use pentosyl radicals.

$Z_1$ to $Z_5$ advantageously are chosen independently of one another from H, OH, methoxy, ethoxy and also 2-hydroxyethoxy, and the flavone glycosides have the structure:

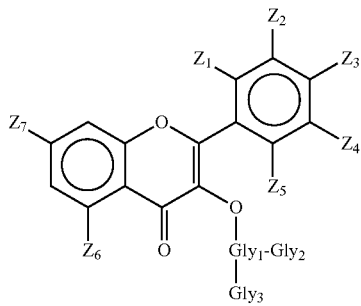

The flavone glycosides of the invention which are of particular advantage are those from the group represented by the following structure:

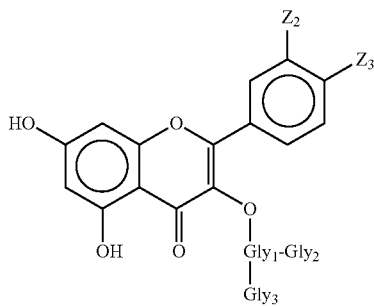

where $Gly_1$, $Gly_2$ and $Gly_3$ independently of one another represent monoglycoside residues or oligoglycoside residues. $Gly_2$ and/or $Gly_3$ may also, individually or together, represent saturations by hydrogen atoms.

Preferably $Gly_1$, $Gly_2$ and $Gly_3$ independently of one another are chosen from hexosyl radicals, in particular rhamnosyl radicals and glucosyl radicals. However, other hexosyl radicals can also be used with advantage where appropriate, examples being allosyl, altrosyl, galactosyl, gulosyl, idosyl, mannosyl and tallosyl. It may also be an advantage in accordance with the invention to use pentosyl radicals.

In the sense of the present invention it is particularly advantageous to choose the flavone glycoside or glycosides from α-glucosylrutin, α-glucosylmyricetin, α-glucosylisoquercitrin, α-glucosylisoquercetin and α-glucosylquercitrin.

Of particular preference in accordance with the invention is α-glucosylrutin.

Also advantageous in accordance with the invention are naringin (aurantiin, naringenin 7-rhamnoglucoside), hesperidin (3',5,7-trihydroxy-4'-methoxyflavanone 7-rutinoside, hesperidoside, hesperetin 7-O-rutinoside), rutin (3,3',4',5,7-pentahydroxyflyvone 3-rutinoside, quercetin 3-rutinoside, sophorin, birutan, rutabion, taurutin, phytomelin, melin), troxerutin (3,5-dihydroxy-3',4',7-tris(2-hydroxyethoxy)flavone 3-(6-(O-(6-deoxy-α-L-mannopyranosyl)-β-D-glucopyranoside)), monoxerutin (3,3',4',5-tetrahydroxy-7-(2-hydroxyethoxy)flavone 3-(6-(O-(6-deoxy-α-L-mannopyranosyl)-β-D-glucopyranoside)), dihydrorobinetin (3,3',4',5',7-pentahydroxyflavonone), taxifolin (3,3',4',5,7-pentahydroxyflavanone), eriodictyol-7-glucoside (3',4',5,7-tetrahydroxyflavanone 7-glucoside), flavanomarein (3',4',7,8-tetrahydroxyflavanone 7-glucoside) and isoquercetin (3,3',4',5,7-pentahydroxyflavanone-3-(β-D-glucopyranoside)).

Further preferred pharmaceutical classes of active substance for a gel matrix of the invention include the following—without making any claim to completeness in the context of the present invention:

antimycotics, such as nafitine, amorrolfine, tolnaftate, ciclopirox nonsteroidal antiinflammatories, such as glycol salicylate, flufenamic acid, ibuprofen, etofenamate, ketoprofen, piroxicam, indomethacin antipruritics, such as polidocanol, isoprenaline, crotamiton local anesthetics, such as lidocaine, benzocaine antipsoriatics, such as ammonium bitumasulfonate keratolytics, such as urea.

Among the active substances, those which should be emphasized as being particularly important for polymer matrices, hydrogels/cataplasms or pads of the invention are the disinfectants or antiseptics.

Substances designated as disinfectants are those suitable for disinfection, i.e., for controlling pathogenic microorganisms, such as bacteria, viruses, spores, microfungi and molds. In general the products are employed on the surface of skin, clothing, equipment, rooms, but also drinking water, foodstuffs, seeds (dressing) and as soil disinfectants.

Disinfectants particularly for local application, such as for wound disinfection, for example, are also referred to as antiseptics.

Disinfectants are defined as substances or compositions which, when used on articles or surfaces, place them in such a condition that they no longer cause any infection. Their action must be bactericidal, fungicidal, virucidal and sporicidal, i.e., the collective term: microbicidal. A bacteriostatic effect is inadequate for disinfectants. In general, therefore, they are pantoxic, i.e., they develop their action against all living cells.

Depending on the intended use, the disinfectants are divided into those for disinfecting laundry, surfaces, instruments, skin and hands, and for stool and sputum disinfection. Disinfectant cleaners are understood as being those disinfectants which also act as cleaning products and, where appropriate, care products.

Taking into account the diverse requirements imposed on disinfectants, such as, for example, broad-spectrum action, short activity times, skin compatibility, low toxicity, materials compatibility, and so on, only certain types of active substance are suitable for the desired use.

1. The most important group of active substances are the aldehydes (formaldehyde, glyoxal, glutaraldehyde). They possess a broad-spectrum action including virus activity and sporicidal action in the case of formaldehyde and glutaraldehyde.

2. Phenol derivatives possess a good bactericidal action, but are not sporicidal. Compared with almost all other active disinfectant substances, they have the advantage of being relatively unaffected by dirt. They are therefore particularly suitable for stool disinfection. Typical representatives are 2-biphenylol and p-chloro-m-cresol (4-chloro-3-methylphenol).

3. Alcohols are characterized by rapid activity, but only at relatively high concentrations of about 40%-80%.

4. The quaternary ammonium compounds, cationic surfactants (invert soaps) and amphoteric surfactants belong to the class of the surfactants. They are characterized by fairly good skin compatibility and materials compatibility and also by odor neutrality. Their spectrum of action, however, is only limited. They include, for example, benzalkonium chloride, cetrimonium bromide, cetylpyridinium chloride (hexadecylpyridinium chloride) and others.

Quaternary ammonium compounds are organic ammonium compounds containing quaternary nitrogen atoms. Quaternary ammonium compounds having a hydrophobic alkyl radical are biocidal; their use is admittedly declining, for toxicological reasons.

Quaternary ammonium compounds are prepared by reacting tertiary amines with alkylating agents, such as methyl chloride, benzyl chloride, dimethyl sulfate, dodecyl bromide, for example, but also ethylene oxide. Depending on the tertiary amine employed, three groups are differentiated:

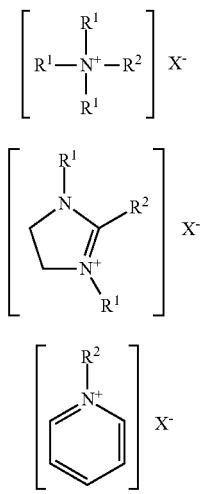

a) linear alkylammonium compounds
b) imidazolinium compounds
c) pyridinium compounds $R^1=CH_3$, $R^2=C_{8-18}$, X=halogen.

The alkylation of tertiary amines having a long alkyl radical and two methyl groups is accomplished particularly easily, and the quaternization of tertiary amines having two long radicals and one methyl group can be carried out using methyl chloride under mild conditions. Amines possessing three long alkyl radicals or hydroxy-substituted alkyl radicals are not very reactive and are preferably quaternized using dimethyl sulfate.

5. Among the halogens, chlorine and iodine possess a certain significance as disinfectants. Chlorine is known from water treatment and pool disinfection and, therewith, its unpleasant properties such as odor and corrosiveness. In spite of the excellent action against bacteria, fungi, spores and viruses, chlorine-containing disinfectants have not found any great use in the human segment, for the abovementioned reasons and on account of the heavy chlorine loss due to organic substances. In contrast, hypochlorites, chloride of lime and chloroisocyanuric acids are still used extensively as industrial disinfectants. Tincture of iodine is used in the medical segment as an antiseptic.

6. Disinfectants based on active oxygen (for example, hydrogen peroxide, peroxyacetic acid) have recently regained some importance.

7. Silver, both alone and in bound form, has a strongly antiseptic action, since the Ag ions contained in the oxide layer of the metal surface exert a blocking effect on the thiol enzymes in the microorganisms. Ag ions are also strongly fungicidal and bactericidal. Thin, bactericidal silver foils are therefore used as a wound dressing material, likewise silver aerosols, silver solutions, silver-containing ointments, tablets and the like as antiseptics and antimycotics.

The silver ions can be used in the form of salts, zeolites, e.g., aluminum silicates, or, preferably, silver glasses.

Aside from the stated active microbicidal substances, a number of microbistatic substances and preservatives (diphenyl ether, carbanilides, acetanilides of aromatic acids and salts thereof) are still on the market for specific use, and are included among disinfectants in the broader sense.

No uniform mode of action of the disinfectants can be discerned. While certain preparations are supposed to act destructively on the cytoplasmic membrane of the bacteria, for others an irreversible blocking of important sulfide bonds in enzymes or of trace elements, by chelation, is assumed.

The invention accordingly further provides for the use of disinfectant products in polymer matrices which comprise
at least one nonionic surfactant and
at least one amino acid and/or amino acid derivative
and at least one disinfectant agent and/or active microbicidal substance.

The nonionic surfactant or surfactants is or are chosen advantageously from the group of the alkyl ethoxylates and/or alkyl propoxylates whose alkyl group is a saturated or unsaturated, straight- or branched-chain alkyl group having (8) 10 to 18, preferably 12 to 14, carbon atoms; they preferably contain per molecule 2 to 15, in particular 5 to 9, and especially 7 ethylene oxide units. Very particular preference is given to isotridecanol ethoxylate and/or fatty alcohol polyglycol ethers.

Advantageously the total amount of nonionic surfactants (one or more compounds) is chosen from the range from 1.0% to 20.0% by weight, preferably from 5.0% to 15.0% by weight, based in each case on the total weight of the matrix.

Advantageous amino acids are, for example, glutamic acid, which is characterized by the following structural formula:

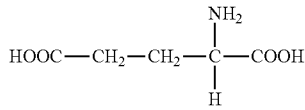

and/or pyrrolidone carboxylic acid (pyroglutamic acid), which is characterized by the following structural formula:

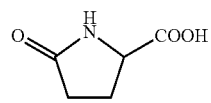

Advantageously the total amount of amino acids (one or more compounds) is chosen from the range from 0.1% to 10.0% by weight, preferably from 0.5% to 2.0% by weight, based in each case on the total weight of the matrix.

The disinfectant agent or agents (active microbicidal substances) are preferably chosen from aldehydes (for example, formaldehyde, glyoxal, glutaraldehyde), phenol derivatives (for example, 2-biphenylol and p-chloro-m-cresol (4-chloro- 3-methylphenol)), alcohols, quaternary ammonium compounds (for example, benzalkonium chloride, cetrimonium bromide, cetylpyridinium chloride (hexadecylpyridinium chloride). Aldehydes and quaternary ammonium compounds are especially preferred in this context.

In one particularly advantageous embodiment the disinfectant systems may further comprise amphoteric surfactants. Amphoteric surfactants are surfactants which possess both acidic and basic hydrophilic groups and which therefore, depending on conditions, behave acidically or basically. Advantageous are, for example, amphoteric surfactants based on aliphatic polyamines having carboxyl, sulfo or phosphono side chains, such as R—NH—(CH$_2$)$_n$—COOH, for example.

Preference is given for example to amphoteric surfactants whose alkyl group is a saturated or unsaturated, straight- or branched-chain alkyl group having 10 to 18, preferably 12 to 14, carbon atoms.

Further of particular advantage are amphoteric surfactants from the group of the amphopropionates, such as, for example, cocobetaineamido amphopropionate, which is characterized by the following structure:

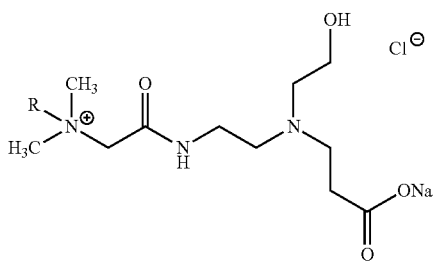

The total amount of amphoteric surfactants (one or more compounds) is advantageously chosen from the range from 1.0% to 10.0% by weight, preferably from 2.0% to 5.0% by weight, based in each case on the total weight of the matrix.

It is advantageous to carry out dilution such that the amount of the individual substances in the solution for use is as follows:

| | |
|---|---|
| nonionic surfactants: | between 0.005% and 1% by weight |
| amino acid: | between 0.0005% and 0.5% by weight |
| optionally, amphoteric surfactants: | between 0.005% and 0.5% by weight |
| disinfectant agents: | between 0.01% and 2.0% by weight |

In addition to the components specified above, the disinfectant systems for such preparations may comprise customary preservatives, dyes, fragrances and/or other customary auxiliaries. It is also possible, however, to use components which develop a (preserving, caring, etc.) action and at the same time provide a certain color and/or a pleasant fragrance.

The amounts of such vehicles and perfume to be employed in each case can be determined easily as a function of the nature of the specific product by the skilled worker, by simple trial.

Also of advantage is the use of disinfectant systems which comprise at least one active microbicidal substance chosen from alkylamines, at least one amino acid and/or amino acid derivative, and at least one quaternary ammonium compound.

With advantage the quaternary ammonium compounds are preferably chosen from benzalkonium chloride, didecyldimethylammonium chloride, cetrimonium bromide and cetylpyridinium chloride (hexadecylpyridinium chloride). The alkylamine is advantageously dodecylbispropylenetriamine.

In accordance with the invention, advantageously, nonionic surfactants are additionally added, chosen with particular advantage from alkyl ethoxylates whose alkyl group is a saturated or unsaturated, straight- or branched-chain alkyl group having 8 to 18, preferably 12 to 14, carbon atoms, and containing preferably per molecule 2 to 15, in particular 5 to 9, especially 7, ethylene oxide units. Very particular preference is given to isotridecanol ethoxylate and/or fatty alcohol polyglycol ethers.

The total amount of nonionic surfactants (one or more compounds) is advantageously chosen from the range from 1.0% to 20.0% by weight, preferably from 5.0% to 15.0% by weight, based in each case on the total weight of the matrix.

Additionally, as agents for disinfection, preservation and antisepsis, a multiplicity of microbicidally active chemical substances or mixtures of these substances is known per se. Microbicidal substances are in general active against the customary spectrum of microorganisms, such as gram-positive bacteria, gram-negative bacteria, mycobacteria, yeasts, fungi, viruses and the like, for example, to a greater or lesser extent, and so normally sufficient disinfection, preservation or antisepsis can be achieved by means of suitable active-substance combinations.

For the purpose of disinfection, preservation and antisepsis a range of active substances are known, especially aldehydes, such as formaldehyde or glutaraldehyde, for example, quaternary ammonium compounds and long-chain amines, phenols or alcohols.

Aldehydes fix residues of blood and protein by means of chemical reaction on the articles to be disinfected, so that following disinfection these articles are difficult to clean. Moreover, they have a comparatively high allergenic potential, and so applications to skin and hands are possible only in low concentrations or else can be contemplated in combination with further active substances, in order to be able to remain—as required—below the sensitization threshold. Higher concentrations of aldehydes are also undesirable on account of their odor, and for this reason as well the concentration is reduced by combination with further active substances.

Quaternary ammonium compounds and long-chain amines are frequently used in surface disinfection and for manual instrument disinfection and to a small extent also in antisepsis of the hands. In comparison to the aldehydes, the odor of these compounds is significantly less unpleasant. There is no chemical reaction with proteins, but there is a physical precipitation of proteins, which can be partially compensated by skillful combination with surfactants. For mechanical disinfection of instruments the quaternary ammonium compounds are not suitable, since owing to the turbulences within the cleaning machine there is severe, unwanted foaming. In the case of surface disinfection, quaternary ammonium compounds show a strong tendency to "attach" to the surfaces; that is, layers of these compounds are developed on the surfaces. A further crucial disadvantage is the restricted spectrum of action of quaternary ammonium compounds, since they act neither sporicidally nor against non-enveloped viruses.

Phenols are on the decline principally on account of their odor, their low level of activity against the polio virus, their in some cases poor degradability, their high lipid solubility in conjunction with strong penetration through the skin, and also toxicology and mutagenicity risks, in virtually all segments of application for disinfectants.

The aliphatic alcohols ethanol, propan-1-ol and propan-2-ol have long been known as active substances for disinfecting skin and hands or for the antisepsis of skin and hands. With disinfectants and antiseptics based on alcohols it is possible with short exposure times of 30 to 60 seconds to obtain germ count reductions of up to 99.9%. A general, brief presentation of the microbicidal activity of alcohols is found in the following book: K. H. Wallhäußer, "*Praxis der Sterilisation, Desinfektion and Konservierung*", G. Thieme Verlag, Stuttgart, New York, 5th edition, pp. 469-474.

Alcohols possess a bactericidal action which increases from methanol to propanol. Use is made in particular of ethanol, n-propanol and isopropanol, the alcohol content of the preparations being situated generally between 50% and 80%. The essential advantage of alcohols is that the onset of action is very rapid. Disadvantages are that they are not active against spores and that the action ends after a very short time, since alcohols evaporate rapidly. Although an antiviral activity is under discussion for alcohols, it is only on the other side of a high concentration limit, which in the case of ethanol is presumed to be about 80%.

It has been found in practice that alcoholic disinfectants and antiseptics are unable, or unable adequately, to destroy viruses and traces of *Bacillus* and *Clostridium* species. Although the freedom of alcoholic solutions from spores can be achieved by filtration, it cannot be completely ruled out in practice that microorganism spores will (subsequently) enter the preparations, for example, during the brief opening of the storage vessels or during dispensing of the products into containers already containing spores. For this reason, when using alcoholic skin and hand antiseptics, there is always a certain risk of an infection caused by spores.

Antiseptics are particularly suitable for treating the skin. Antiseptics display a very good activity against dermatophytes and in particular are distinguished, surprisingly, by the fact that they have a very good activity with respect to viruses.

The constituents of antiseptics act synergistically in respect of their antimicrobial and antiviral properties, i.e., act super-additively in a significant way.

Also advantageous, accordingly, is the use of a preparation comprising

| | |
|---|---|
| (a) 42%-47% by weight | of 1-propanol |
| (b) 22%-27% by weight | of 2-propanol |
| (c) 4%-6% by weight | of ethanol |
| (d) at least 20% by weight | of water |
| (e) not more than 0.0001% by weight | of substances which under standard conditions are in the form of solids |
| (f) no effective content | of further substances which are distinguished by virucidal properties | as an antiseptic, particularly its use for controlling or inactivating the HIV virus or the hepatitis B virus.

Particularly suitable as an antiseptic is, in turn, chlorhexidine, the international nonproprietary name for 1,1'-hexamethylenebis[5-(4-chlorophenyl)biguanide], the antiseptic used being the dihydrochloride, diacetate and digluconate.

In the context of the present invention it also has surprisingly emerged that the formulations of the invention are also especially suitable for the use of active substances which have a positive influence on skin condition. Thus it has been found that active substances for positively influencing aging skin, which reduce the formation of wrinkles or even lessen existing wrinkles. Particularly preferred active substances are therefore considered to be bioquinones, especially ubiquinone, Q10, creatine, creatinine, carnitine, acetylcarnitine, biotin, isoflavone and isoflavonoids, genistein, arctiine, cardiolipine, lipoic acid, anti-freezing proteins, hop extracts and hop-malt extracts, and/or substances which promote restructuring of the connective tissue, isoflavonoids and isoflavonoid-containing plant extracts such as soya extracts and clover extracts, for example, which can be used very effectively in the matrices of the invention.

Also it has been found that the matrix is particularly suitable for using active substances for assisting skin functions in the case of dry skin, such as vitamin C, biotin, carnitine, creatine, creatinine, propionic acid, glycerin, green tea extracts, eucalyptus oil, urea and mineral salts such as NaCl, marine minerals and also osmolytes such as, for example, taurine, inositol, betaine, and quaternary ammonium compounds.

Similarly, the incorporation of active substances for alleviating or positively influencing irritative skin conditions proved advantageous, whether for sensitive skin in general or for skin irritated by noxae (UV light, chemicals). Active substances to be mentioned here are substances such as sericosides, various extracts of liquorice, licochalcone A, silymarin and/or silyphos, dexpanthenol, ethanol, inhibitors of prostaglandin metabolism, particularly of cyclooxygenase, and of leukotriene metabolism, particularly of 5-lipoxygenase, but also of the 5-lipoxygenase inhibitor protein, FLAP.

The incorporation of pigmentation modulators also proved advantageous. Active substances to be mentioned here are substances which reduce the pigmentation of the skin and so lead to a cosmetically desired lightening of the skin and/or which reduce the incidence of age spots and/or lighten existing age spots, such as tyrosine sulfate, dioic acid (8-hexadecene-1,16-dicarboxylic acid), lipoic acid and liponamide, various extracts of liquorice, kojic acid, hydroquinone, arbutin, fruit acids, especially alpha-hydroxy acids (AHAs), bearberry (*Uvae ursi*), ursolic acid, ascorbic acid, green tea extracts, aminoguanidine and/or pyridoxamine.

In the same way the matrices of the invention proved to be an outstanding basis for active substances which bring about increased/more rapid tanning of the skin (advanced glycation end products (AGE)), lipofuscins, nucleic acid oligonucleotides, purines and pyrimidines, NO-releasing substances, whether with or without the influence of UV light.

The polymer matrix will contain the active substance or substances in amounts of 0-35% by weight, preferably 0-15% by weight, very preferably 0.02%-2%.

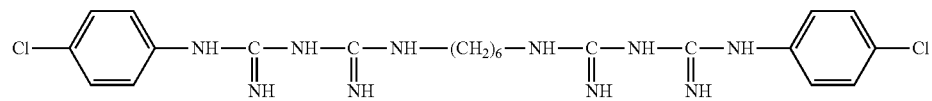

For the prophylaxis of oxidative and degenerative damage and in particular for the treatment of such damage it has surprisingly been found advantageous to add antioxidants to the cosmetic matrices/pads. The antioxidants are advantageously selected from amino acids, e.g. glycine, lysine, arginine, cysteine, histidine, tyrosine, tryptophan, and their derivatives (as salt, ester, ether, sugar, nucleotide, nucleoside, peptide and/or lipid compound), imidazoles, e.g. urocanic acid, and their derivatives as salt, ester, ether, sugar, nucleotide, nucleoside, peptide and/or lipid compound, peptides such as D,L-carnosine, D-carnosine, L-carnosine, anserine and derivatives thereof, e.g., as salt, ester, ether, sugar, thiol, nucleotide, nucleoside, peptide and/or lipid compound, carotenoids, carotenes, e.g., α-carotene, β-carotene, ψ-lycopene, phytoene, and derivatives thereof, e.g. as salt, ester, ether, sugar, nucleotide, nucleoside, peptide and/or lipid compound, chlorogenic acid and derivatives thereof, as salt, ester, ether, sugar, thiol, nucleotide, nucleoside, peptide and/or lipid compound, aurothioglucose, propylthiouracil and other thiols, e.g. thioredoxin, lipoic acid, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters, and also salts thereof, dilauryl thiodipropionate, distearyl thiodipropionate, thiodipropionic acid and derivatives thereof, as salt, ester, ether, sugar, thiol, nucleotide, nucleoside, peptide and/or lipid compound, and also sulfoximine compounds, e.g. homocysteine sulfoximine, buthionine sulfones, penta-, hexa-, heptathionine sulfoximine, in very low tolerated doses, e.g., pmol to μmol/kg. Additionally (metal) chelating agents, e.g., apoferritin, desferral, lactoferrin, α-hydroxy fatty acids, palmitic acid, phytic acid, and derivatives thereof, as salt, ester, ether, sugar, thiol, nucleotide, nucleoside, peptide and/or lipid compound, α-hydroxy acids, e.g., citric acid, lactic acid, malic acid, humic acid, bile acid, bile extracts, bilirubin, biliverdin, melanin, EDTA, EGTA and derivatives thereof, unsaturated fatty acids and their derivatives, e.g., γ-linolenic acid, linoleic acid, oleic acid, folic acid and derivatives thereof, furfurylidenesorbitol and its derivatives, ubiquinone, ubiquinol, plastoquinone and derivatives thereof, as salt, ester, ether, sugar, thiol, nucleotide, nucleoside, peptide and lipid compound, vitamin C and derivatives, e.g., ascorbyl palmitate, Mg-ascorbyl phosphate, ascorbyl acetate, tocopherols and derivatives, e.g. vitamin E acetate, Trolox®, and also phenolic compounds and plant extracts comprising them, such as flavonoids, for example, e.g., glycosylrutin, ferulic acid, caffeic acid, furfurylideneglucitol, butylated hydroxytoluene, butylhydroxyanisole, nordihydroguaiacic acid, nordihydroguaiaretic acid, trihydroxybutyrophenone and derivatives thereof, as salt, ester, ether, sugar, nucleotide, nucleoside, peptide and lipid compound, uric acid and derivatives thereof, mannose and derivatives thereof, as salt, ester, ether, sugar, thiol, nucleotide, nucleoside, peptide and lipid compound, zinc and its derivatives, e.g. ZnO, ZnSO₄, selenium and its derivatives, e.g. selenium methionine, ebselen, stilbenes and derivatives thereof, e.g., stilbene oxide, trans-stilbene oxide, and the derivatives that are suitable in accordance with the invention, as salt, ester, ether, sugar, thiol, nucleotide, nucleoside, peptide and/or lipid compound, of these stated active substances.

For use as patches, the gel matrices of the invention are pressed, rolled or the like as a layer onto a release medium made of paper, film or the like and are laminated on the reverse with any desired backing material such as, for example, a polymer film, textiles or the like. With particular preference in accordance with the invention the gel matrices are applied in the hot state by a metering pump to a backing material, and with very particular preference are configured in a three-dimensional form by means of corresponding cavities in the presses or roller mechanisms. The shape of the patches produced is determined by the shape of the cavities and is not subject to any restriction; it may, for example, be ellipsoidal with edges which flatten off, or may, for example, be angular in configuration.

With particular advantage the gel matrix of the invention is applied on a flexible cover layer, particularly when used as a patch. A corresponding patch is constructed from a backing such as films, nonwovens, wovens, foams, etc., the adhesive matrix, and liner film, liner paper or release paper in order to protect the adhesive matrix prior to the use of the patch.

In a further preferred embodiment of the invention, backings used are polymer films, nonwovens, wovens and combinations thereof. Backing materials available for selection include polymers such as polyethylene, polypropylene, polyesters, polyethers, polyether-ester copolymers and polyurethane or else natural fibers.

In summary it can be maintained that suitable backing materials encompass all rigid and elastic sheet-like structures of synthetic and natural raw materials. Preference is given to backing materials which can be employed such that they fulfill properties of a functional dressing. Listed by way of example are textiles such as wovens, knits, lays, nonwovens, laminates, nets, films, foams and papers. In addition it is also possible for these materials to be pretreated and/or aftertreated. Customary pretreatments are corona and hydrophobicization; common after-treatments are calendering, heat-treating, laminating, punching and enveloping.

It is particularly advantageous if the backing material is sterilizable, preferably γ(gamma)-sterilizable.

Very particularly preferred backing materials in accordance with the invention are those which have good oxygen, air and water vapor permeability, which have been provided point-wise with the adhesive polymer matrix by screen printing or analogous methods, and which outwardly overlap the applied gel matrix at the side edges. Matrices of the invention manufactured in this form can be affixed self-adhesively to parts of the body that are under severe mechanical stress, such as elbows or knee joints, where the inherent adhesion of the hydrogels/cataplasms is no longer sufficient for durable application.

The stated properties of the adhesive matrix suggest its use in particular for medical products, especially patches, medical fastenings, wound coverings, orthopedic or phlebological bandages, and dressings.

The use of the self-adhesive polymer matrix, composed of a polyacrylic acid polymer, agar-agar, glycerin and water, in patches, strips, wound coverings and/or bandages, in particular, is an extremely simple, skin-compatible possibility for wound care or skincare. The patches, wound coverings or bandages thus equipped exhibit an individually adjustable consistency and bond strength and are extremely inexpensive as compared with known medical materials. The polymer matrix can be employed alone or in combination with suitable, coated backing materials. It is possible accordingly to produce products which can also be employed on moving body parts, such as fingers or elbows, for example.

Also particularly suitable is the use of the polymer matrices in which water-soluble or hydrophobic active substances have been incorporated as active substance patch systems or TTS for the controlled delivery of active substance to the skin.

The use of the self-adhesive polymer matrix is to be regarded with advantage in particular as an active substance administration form for topical or buccal use or as a component of a TTS, particularly of a monolithic TTS.

Through the use, for example, of menthol on a fleece material coated by screen printing it is possible to produce a patch with the polymer matrix, which results in a cooling effect on minor burns as a result of the evaporation, the delivery of menthol and/or water. The use of the self-adhesive polymer matrix comprising menthol as an active substance for use in the case of skin burns is therefore preferred.

Where nonsteroidal antiinflammatories are used as active substances, the polymer matrix is advantageously appropriate for treating disorders of the rheumatic kind.

The use of essential oils as active substances likewise allows the polymer matrix to be used in respect of cold-type diseases and also for aromatherapy.

By virtue of its simple construction the matrix is suitable for producing patch systems or TTS quickly, simply and at low cost. As a result of the possibility of incorporating active substances, moreover, the breadth of application of such patch systems is greatly enhanced and the profitability in production is increased.

Finally the gel matrix can be enveloped with an anti-adhesive backing material, such as siliconized paper, or provided with a wound pad or a cushion. On its self-adhesive side which later faces the skin, the patch of the invention is lined over its whole width, until used, usually with an anti-adhesive backing material. This protects the self-adhesive layer from the gel matrix's adhesive, which possesses good skin compatibility and which has preferably been applied by a transfer method, and additionally stabilizes the product as a whole. The lining can be designed, in a known way, in once piece or, preferably, in two parts.

Further embodiments may be such that between the reverse of the matrix and the lining backing there is a second matrix possessing higher active-substance solubility, as a reservoir. Instead of a second matrix and backing, this might also be a thermoformed film with pure active substance.

Located on part (e.g., at the edge) of the adhesive side of the matrix is a second matrix possessing high bond strength for the purpose of additional fixing, but possessing insufficient active-substance solubility.

The active substance-free matrix is located between two non-anchoring films and is utilized for fixing. The active substance-free matrix could also serve (with or without a wound pad) as an adhesive layer for a simple wound/sticking plaster.

The use of the polymer matrix as a medical plaster system, as a patch, pad, wound pad or bandage is suitable particularly in a flat embodiment with a total area of 0.2 to 1000 cm$^2$. With this, for example, small (0.2-2 cm$^2$) burn regions of the skin are covered, or large regions (up to 1000 cm$^2$) for the purpose of cooling or in the case of rheumatic complaints.

Preference is also given in this context to the use of the self-adhesive polymer matrix in a two- or three-dimensional embodiment with a polymer matrix weight fraction of 0.1 to 1000 g, in particular of 500 g. The shape in this case may be round, oval, angular or designed in accordance with the sections of the skin.

DETAILED DESCRIPTION OF THE INVENTION

The examples which follow illustrate the invention without restricting it. The tables below list gel matrices of the invention. The mass fractions reported are based on the overall mass of the matrix.

Examples I-III

| Constituent | I | II | III |
|---|---|---|---|
| Water | 69.90% | 59.90% | 49.90% |
| Agar agar | 2.00% | 2.00% | 2.00% |
| Glycerin | 20.00% | 30.00% | 40.00% |
| Carbopol 980 | 8.00% | 8.00% | 8.00% |
| NaOH | 0.10% | 0.10% | 0.10% |

Examples I-III exhibit similar adhesion with a constant polyacrylic acid content and with a likewise constant agar agar content, but increasing cohesiveness/elasticity with increasing glycerin content.

Examples IV-VI

| Constituent | IV | V | VI |
|---|---|---|---|
| Water | 59.90% | 55.90% | 51.90% |
| Agar agar | 2.00% | 2.00% | 2.00% |
| Glycerin | 30.00% | 30.00% | 30.00% |
| Carbopol 980 | 8.00% | 12.00% | 16.00% |
| NaOH | 0.10% | 0.10% | 0.10% |

Examples IV-VI exhibit analogous cohesiveness/elasticity with a constant agar agar and glycerin content and increasing adhesion with a simultaneously increasing polyacrylic acid content.

Examples VII-IX

| Constituent | VII | VIII | IX |
|---|---|---|---|
| Water | 52.1997% | 56.1997% | 58.2000% |
| Sorbitol | 15.7000% | 15.7000% | 15.7000% |
| Agar agar | 2.0000% | 2.0000% | 2.0000% |
| Glycerin | 15.0000% | 15.0000% | 15.0000% |
| Carbopol 980 | 8.0000% | 8.0000% | 8.0000% |
| NaOH | 0.1000% | 0.1000% | 0.1000% |
| Propanediol | 5.0000% | — | — |
| FA Blue No-1 | 0.0003% | 0.0003% | — |
| Menthol | 1.0000% | — | — |
| Dexpanthenol | 1.0000% | — | — |
| Capsicum extract | — | 3.0000% | — |
| Chlorhexidine digluconate | — | — | 1.0000% |

In every respect the formulations of the invention are completely satisfactory preparations which are distinguished by an outstanding action. When the matrices of the invention are used with an effective content of active substances used in accordance with the invention it is possible to achieve effective treatment, but also prophylaxis, of inflammatory skin conditions—including atopic eczema—and/or skin protection in the case of dry skin which has been determined as being sensitive. The active substance of the invention or the topical dermatological preparations containing an effective amount of active substance of the invention also serve surprisingly, however, for soothing sensitive or irritated skin.

Examples X-XII

| Constituent | X | XI | XII |
|---|---|---|---|
| Water | ad 100% | ad 100% | ad 100% |
| Sorbitol | 15.7% | 15.0% | 15.7% |
| Agar-agar | 2.0% | 2.0% | 2.0% |
| Glycerin | 15.0% | 15.0% | 15.0% |
| Carbopol 980 | 8.0% | 8.0% | 8.0% |
| Creatin | 0.2% | 0.25% | 0.1% |
| NaOH | 0.1% | 0.1% | 0.1% |
| Propanediol | 5.0% | — | — |
| Menthol | 1.0% | — | — |
| Dexpanthenol | 1.0% | — | — |
| Capsicum extract | — | 3.0% | — |
| Chlorhexidine digluconate | — | — | 1.0% |

In every respect the formulations of the invention are completely satisfactory preparations which are characterized by an outstanding action. When the active substances used in accordance with the invention or cosmetic or topical dermatological preparations are used with an effective content of active substances used in accordance with the invention it is possible to achieve effective treatment, but also prophylaxis, of inflammatory skin conditions—including atopic eczema—and/or skin protection in the case of dry skin which has been determined as being sensitive. The active substance of the invention or cosmetic or topical dermatological preparations containing an effective amount of active substance of the invention also serve surprisingly, however, for soothing sensitive or irritated skin.

The following preparations have proved to be particularly suitable for use for age spots:

Examples XIII-XV

| Constituent | XIII | XIV | XV |
|---|---|---|---|
| Water | ad 100% | ad 100% | ad 100% |
| Sorbitol | 15.7% | 15.7% | 15.7% |
| Agar-agar | 2.0% | 2.0% | 2.0% |
| Propanediol | 5.0% | 5.0% | 5.0% |
| Glycerin | 15.0% | 15.0% | 15.0% |
| Carbopol 980 | 8.0% | 8.0% | 8.0% |
| NaOH | 0.1% | 0.1% | 0.1% |
| Creatine | — | — | 0.5% |
| Liponamide | 0.05% | 0.1% | — |

The following preparations have proved to be particularly suitable for use for inflammatory and irritative skin conditions, in particular for shaving burn and sunburn:

Examples XVI-XVII

| Constituent | XVI | XVII | XVIII |
|---|---|---|---|
| Water | ad 100% | ad 100% | ad 100% |
| Sorbitol | 15.7% | 15.7% | 15.7% |
| Agar-agar | 2.0% | 2.0% | 2.0% |

-continued

| Constituent | XVI | XVII | XVIII |
|---|---|---|---|
| Propanediol | 5.0% | 5.0% | 5.0% |
| Glycerin | 15.0% | 15.0% | 15.0% |
| Carbopol 980 | 8.0% | 8.0% | 8.0% |
| NaOH | 0.1% | 0.1% | 0.1% |
| Liquorice extract | 0.01% | 0.05% | — |

The following preparations have proved to be particularly suitable for use for age-related wrinkles:

Examples XIX-XXI

| Constituent | XIX | XX | XXI |
|---|---|---|---|
| Water | ad 100% | ad 100% | ad 100% |
| Sorbitol | 15.7% | 15.7% | 15.7% |
| Agar-agar | 2.0% | 2.0% | 2.0% |
| Propanediol | 5.0% | 5.0% | 5.0% |
| Glycerin | 15.0% | 15.0% | 15.0% |
| Carbopol 980 | 8.0% | 8.0% | 8.0% |
| NaOH | 0.1% | 0.1% | 0.1% |
| Q10 | — | — | 0.1% |
| Creatine | 0.5% | 0.1% | — |

What is claimed is:

1. A self-adhesive polymer matrix comprising self-adhesive effective amounts of (a) at least one polymer which forms a gel in water, (b) water, (c) a sea algae extract, and (d) at least one alcohol selected from monohydric and polyhydric alcohols.

2. The polymer matrix of claim 1, wherein (a) comprises at least one polyacrylic acid polymer.

3. The polymer matrix of claim 2, wherein the at least one polyacrylic acid polymer comprises an acrylate-alkyl acrylate copolymer having the structure:

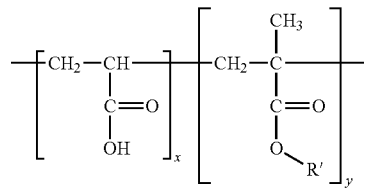

where R' is an alkyl radical and x and y indicate the stoichiometric fraction of the respective comonomers.

4. The polymer matrix of claim 2, wherein the at least one polyacrylic acid polymer comprises a copolymer of a $C_{10-30}$ alkyl acrylate and one or more of acrylic acid, methacrylic acid and esters thereof, which copolymer is crosslinked with an allyl ether of sucrose or with an allyl ether of pentaerythritol.

5. The polymer matrix of claim 1, wherein the matrix comprises from 2% to 55% by weight of (a), based on a total weight of the matrix.

6. The polymer matrix of claim 1, wherein (c) comprises agar-agar.

7. The polymer matrix of claim 1, wherein (c) comprises carrageenan.

8. The polymer matrix of claim 1, wherein (c) comprises at least one of alginic acid and a salt or ester thereof.

9. The polymer matrix of claim 1, wherein the matrix comprises from 0.1% to 15% by weight of (c), based on a total weight of the matrix.

10. The polymer matrix of claim 1, wherein (d) comprises at least one of glycerin and propanediol.

11. The polymer matrix of claim 10, wherein the matrix comprises from 1% to 85% by weight of (d), based on a total weight of the matrix.

12. The polymer matrix of claim 1, wherein the matrix further comprises (e) at least one of a pharmaceutically active substance and a dermatological or cosmetic substance.

13. The polymer matrix of claim 12, wherein (e) comprises at least one active substance selected from dexpanthenol, capsaicin, lidocaine and salts thereof, menthol, camphor, ibuprofen and salts thereof, ketoprofen, eucalyptus oil, peppermint oil, chlorhexidine and thereof, silver or silver compounds, jojoba oil and aloe vera.

14. The polymer matrix of claim 12, wherein (e) comprises at least one substance selected from disinfectants and antiseptics.

15. The polymer matrix of claim 12, wherein (e) comprises at least one of creatine, creatinine, alpha-glucosylrutin, taurine, serinol, isoserinol, liquorice aqua PU, liquorice PU, silymarin, silyphos, lipoic acid, liponamide, green tea extract, vitamin C, 8-hexadecene-1,16-dicarboxylic acid, isoflavone, isoflavonoid-containing plant extracts, ubiquinone Q10, sericosides, tyrosine sulfate, jojoba oil, and aloe vera.

16. A patch, a cosmetic or dermatological matrix or a pad which comprises the polymer matrix of claim 1.

17. A two-dimensional product which comprises the polymer matrix of claim 1 and has a total area of from 0.2 to 1000 cm$^2$.

18. A two-dimensional or three-dimensional product which comprises from 0.1 to 1,000 g of the polymer matrix of claim 1.

19. A medical patch which comprises the polymer matrix of claim 1.

20. A bandage which comprises the polymer matrix of claim 1.

* * * * *